United States Patent [19]

Dougherty et al.

[11] Patent Number: 5,145,989
[45] Date of Patent: Sep. 8, 1992

[54] RECOVERY OF ACRYLIC ACID AND/OR ETHYL ACRYLATE FROM BLACK ACID

[75] Inventors: Edward F. Dougherty, League City, Tex.; Paul James L., Summit, N.J.

[73] Assignee: Hoechst Celanese Corporation, Somerville, N.J.

[21] Appl. No.: 73,782

[22] Filed: Jul. 14, 1987

[51] Int. Cl.⁵ .................... C07C 57/04; C07C 67/04; C07C 67/11; C07C 69/54
[52] U.S. Cl. .................... 560/205; 203/63; 203/66; 203/95; 203/96; 203/DIG. 21; 560/216; 560/217; 560/218; 562/513; 562/598; 562/599; 562/600
[58] Field of Search ............ 560/205, 216, 217, 218, 560/212; 562/598, 600, 513, 599; 203/DIG. 21, 63, 66, 95, 96

[56] References Cited

U.S. PATENT DOCUMENTS

| | | | |
|---|---|---|---|
| 3,539,621 | 11/1970 | Cipollone et al. | 560/217 |
| 3,894,076 | 7/1975 | Van Duyne et al. | 560/217 |
| 3,951,756 | 4/1976 | Dirks et al. | 203/95 |
| 4,490,553 | 12/1984 | Chase et al. | 560/218 |

Primary Examiner—Vivian Garner
Attorney, Agent, or Firm—D. R. Cassady

[57] ABSTRACT

Black acid or the sulfuric acid residue obtained in the manufacture of ethyl acrylate by reaction of ethylene and acrylic acid in the presence of sulfuric acid is heated and distilled in the presence of a solvent for recovery of acrylic acid and ethyl acrylate.

6 Claims, No Drawings

RECOVERY OF ACRYLIC ACID AND/OR ETHYL ACRYLATE FROM BLACK ACID

BACKGROUND OF THE INVENTION

1. Field of the Invention

The present invention relates to a method for recovering lost ethyl acrylate potential (EAP) and, more particularly, to the recovery of acrylic acid and/or ethyl acrylate from spent black acid obtained in the production of ethyl acrylate by reaction of ethylene, acrylic acid and sulfuric acid.

2. Description of the Prior Art

Ethylenically unsaturated organic compounds, such as acrylic acid, methacrylic acid, methacrylic esters, acrylate esters, and the like, are widely used in the production of homopolymers and copolymers. These homopolymers and copolymers, produced readily through the polymerization of the available double bonds of the organic compounds, are widely used in paints, coatings, lacquers and the like. The olefinic activity of the ethylenically unsaturated organic compounds, makes the polymerized products highly useful for many purposes.

Processes for the production of ethyl acrylate by the interaction of acrylic acid with ethylene in the presence of a sulfuric acid catalyst are well known. As examples see U.S. Pat. No. 3,703,539, issued Nov. 21, 1972, to DiLiddo; U.S. Pat. No. 3,539,621, issued Nov. 10, 1970, to Cipollone et al.; U.S. Pat. No. 3,894,076, issued Jul. 8, 1975, to Van Duyne et al.; and U.S. Pat. No. 4,490,553, issued Dec. 25, 1984, to Chase et al., all of which are incorporated by reference. In these and other references, the reaction is believed to involve the formation of intermediate sulfates from the reaction of ethylene with sulfuric acid. These sulfates further react with acrylic acid to form ethyl acrylate and product mixtures of unreacted ethylene, acrylic acid and sulfuric acid residue which must be recycled to the reactor tower. The product mixture is thus sent to a distillation train comprising a recovery distillation tower, a light ends distillation tower and finishing tower, all of which are conventional. In the recovery tower, the mixture is distilled under vacuum to obtain light ends of crude ethyl acrylate which are passed to a light ends distillation column where a partially purified ethyl acrylate bottoms product is sent to a finishing distillation tower for recovery of substantially pure ethyl acrylate. The bottoms product from the recovery distillation tower is a sulfuric acid residue or black acid stream containing free sulfuric acid, ethyl hydrogen sulfate, diethyl sulfate, lactone polyester, acrylic acid and ethyl acrylate. The sulfuric acid residue or black acid stream is removed as bottoms residue from the recovery distillation tower and then returned to the reactor tower to repeat the cycle. During the ethylene-acrylic acid reaction, black acid builds up in viscosity and to maintain proper viscosity values, which allow favorable use of process equipment and not retard reaction rates, some of the black acid is periodically purged from the system, usually about 1 to 5 wt. %, and new reactants are added. The purged or blow down material, which is rich in ethyl acrylate potential, is reprocessed for sulfur recovery. During the reprocessing of the spent black acid, the ethyl acrylate potential (EAP) is thus lost. Improvement in ethyl acrylate yields would be substantially increased if the EAP could be recovered.

SUMMARY OF THE INVENTION

The present invention is directed to the recovery of ethyl acrylate potential from spent black acid by forming a mixture of black acid with a solvent selected from the group of water, a lower alkanol of 1 to 4 carbon atoms, or mixtures thereof, heating and distilling the mixture, and thereafter recovering acrylic acid and ethyl acrylate.

DESCRIPTION OF THE INVENTION

In carrying out the method of the invention, black acid as obtained in the manufacture of ethyl acrylate by reaction of ethylene, acrylic acid and sulfuric acid is mixed with a solvent such as water, a lower alkanol or a mixture thereof, and then heated and distilled at temperatures within the range of about 50° C. to 250° C., preferably about 120° C. to 170° C., to vaporize ethyl acrylate and acrylic acid from the mixture for recycle to the ethylene-acrylic acid reactor tower or subsequent separation and recovery by fractionation.

While the chemistry of the many and complex reactions which occur during the method of the invention is not fully understood, experiments and observations allow some of the following postulations:

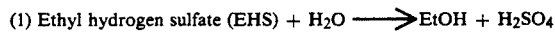

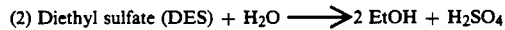

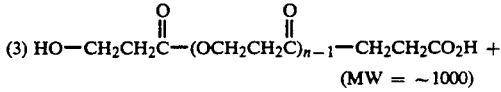

Allowing the following reaction to proceed:

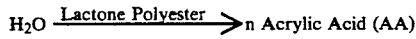

Additional ethanol may be added if insufficient EtOH is not generated by reactions (1) and (2). Again, while the mechanism of the present invention is not clearly understood, it is believed that the sulfuric acid in the black acid stream becomes attached to acrylic acid, and to some degree ethyl acrylate, through hydrogen bonding. Since water in the system is removed in the recovery distillation tower, the sulfuric acid becomes even more strongly attached to acrylic acid which, in fact, acts as a base. However, when a solvent such as water, a lower alkanol, or mixtures thereof, is subsequently added to the black acid stream, it frees acrylic acid and ethyl acrylate and thereby permits their recovery by simple distillation. In the absence of water or the alkanol solvent, high temperatures are ineffective for separating the sulfuric acid residue or black acid stream from ethyl acrylate and acrylic acid.

The heating and distillation can be conducted at atmospheric pressure or the pressure may be reduced or increased above atmospheric. In general, the pressure will range from 50 mm Hg absolute up to about 3 atmospheres, preferably about 1 atmosphere. The distillation can be conducted in a batch, continuous or semi-continuous operation. The time of distillation will vary depending on the temperature and pressure variables, however, it generally has been found that in batch type operations employing a stirred reactor good rates of reaction are obtained within six hours or less.

The solvent used in accordance with the invention is water, a lower alkanol of 1 to 4 carbon atoms, such as methanol, ethanol, propanol or butanol, or an aqueous mixture of the alkanol containing up to about 70% by weight of water, and preferably about 20 to 60 by weight of water. The volume of solvent per volume of black acid charge to the heating and distillation zone will depend on the concentration of sulfuric acid and heavy ends (metal salts of dibasic acids) in the black acid residue stream. Typically, approximately 40 to 50 wt. % of the black acid residue is ethyl acrylate potential (EAP) material comprising acrylic acid, ethyl acrylate, ethanol, ethyl hydrogen sulfate and some diethyl sulfate, whereas about 40 wt. % of the stream is sulfuric acid (determined as wt. % sulfur) and about 10 wt. % is the very heavy ends material. Accordingly, the volume ratio of solvent to feedstock will generally vary within the range of from about 1 to 1 to about 30 to 1 or higher, the preferred solvent to feedstock ratios being determined generally by selection and trial in accordance with well known engineering procedures therefor.

The method of the invention not only provides an effective means for recovery of lost ethyl acrylate value, such as acrylic acid and/or ethyl acrylate, but offers the further advantage of providing a means whereby sulfuric acid can be recycled for reaction with acrylic acid and ethylene. Additionally, since butyl acrylate is prepared by a similar and/or butyl alcohol process involving reaction of acrylic acid with butylene/in the presence of a sulfuric acid catalyst, lost butyl acrylate potential (BAP) can be recovered in the same manner from the spent black acid stream.

The following examples illustrate the best mode now contemplated for carrying out the invention.

EXAMPLE 1

Ten ml of water was added to a flask containing 30 grams of Black Acid (BA) containing approximately 40 to 50 wt. % acrylic acid species as free acrylic acid, lactone (polyester) polymer ( MW=1000) and ethyl acrylate. The remaining portion of the BA, about 50 to 60 wt. % was sulfuric acid species as ethyl hydrogen sulfate, diethyl sulfate and free sulfuric acid. The mixture was heated and distilled at 120°–160° C. under 1 atmosphere of pressure for 42 minutes during which time two phases were distilled overhead. The upper phase contained approximately 6 ml of EAP and the lower phase contained water and acrylic acid. In the same experiment under the same conditions, the remaining black acid in the flask was mixed with an additional 30 ml of water and distillation was continued for 35 minutes more to recover ethyl ether and 2.9 grams of ethyl acrylate from the upper phase and 9.1 grams of acrylic acid from the lower phase. The total overhead volume was approximately 20 ml.

EXAMPLE 2

Sixty grams of BA having the composition of Example 1 and 10 ml of water were mixed together in a flask and heated and distilled at 93° C. under 1 atmosphere pressure. After 10 minutes, 6.4 grams of ethyl acrylate and 5.4 grams of acrylic acid were recovered as overhead. At this point, the flask was cooled and 10 ml of ethanol was slowly added to the flask and distillation continued at 83° C. After about 10 minutes, about 1.76 grams of ethyl acrylate and 15.4 grams of acrylic acid were recovered as overhead. At this point, the pot material became viscous and 10 ml of water and 10 ml of ethanol were added to reduce its viscosity and distillation was continued. In total, 9.4 grams of ethyl acrylate and 20.4 grams acrylic acid were thereafter recovered as overhead.

EXAMPLE 3

Using the BA of Example 1, a series of experiments were carried out at 1 atmosphere pressure with a pot temperature of about 120° to 170° C. Table 1 below illustrates the results obtained when either water or an aqueous mixture of water and ethanol is mixed with BA and heated and distilled at 120°–170° C. under 1 atmosphere of pressure.

TABLE I

| EXAMPLE | CHARGE (gm) | | | PRODUCTION (gm) | | | % EAP RECOVERED (1) |
|---|---|---|---|---|---|---|---|
| | BA | H$_2$O | EtOH | ETHER | ETHYL ACRYLATE | ACRYLIC ACID | |
| 1 | 30 | 10 | — | (4) | 2.9 | 9.1 | 100 |
| 2 | 60 | 20 | 10 | (4) | 9.4 | 20.4 | 124 |
| 3 | 747.5 | 100 | 300 | 51 (17%)(2) | 223.9 | — | 74.9 |
| 4 | 725.0 | 100 | — | — | 120 | — | 16.5(3) |
| 5 | 607.0 | 150 | 150 | 13.4 (8.9%)(2) | 184.9 | — | 76.1 |

(1) Based on the assumption that 40% of the spent BA is EAP.
(2) Based on EtOH charged; however, ether is made without addition of EtOH.
(3) Run terminated because of leak.
(4) Ether not measured.

What is claimed is:

1. In a method for producing ethyl arcylate by reacting ethylene and acrylic acid in the presence of sulfuric acid to obtain ethyl acrylate an a sulfuric acid residue containing sulfuric acid, ethyl hydrogen sulfate, diethyl sulfate, acrylic acid, ethyl acrylate and lactone polyesters of acrylic acid, the improvement comprising forming a mixture of said sulfuric acid residue with a solvent selected from the group consisting of water, a lower alkanol having 1 to 4 carbon atoms, or an aqueous mixture of said alkanol; heating and distilling said mixture at temperatures within the range of about 50° C. to 250° C. at pressures of about 30 mm Hg absolute up to 3 atmospheres to vaporize acrylic acid and ethyl acrylate, and thereafter recovering acrylic acid and ethyl acrylate.

2. The method of claim 1 wherein the heating and distillation is carried out at temperatures of about 120° C. to 170° C. at a pressure of about 1 atmosphere.

3. The method of claim 1 wherein the solvent is water.

4. The method of claim 1 wherein the solvent is a lower alkanol having 1 to 4 carbon atoms.

5. The method of claim 1 wherein the solvent is an aqueous mixture of said alkanol containing up to about 70 wt. % water.

6. The method of claim 5 wherein the alkanol is ethanol.

* * * * *